(12) United States Patent
Guillemont et al.

(10) Patent No.: US 7,790,894 B2
(45) Date of Patent: *Sep. 7, 2010

(54) MYCOBACTERIAL INHIBITORS

(75) Inventors: Jérôme Emile Georges Guillemont, Ande (FR); Elisabeth Therese Jeanne Pasquier, Le Neubourg (FR); David Francis Alain Lancois, Louviers (FR)

(73) Assignee: Janssen Pharmaceutica NV (BE)

( * ) Notice: Subject to any disclaimer, the term of this patent is extended or adjusted under 35 U.S.C. 154(b) by 395 days.

This patent is subject to a terminal disclaimer.

(21) Appl. No.: 11/422,152

(22) Filed: Jun. 5, 2006

(65) Prior Publication Data
US 2007/0299106 A1   Dec. 27, 2007

(30) Foreign Application Priority Data
Jan. 29, 2004   (EP) .................................. 04075286

(51) Int. Cl.
C07D 215/00  (2006.01)
C07D 215/12  (2006.01)
C07D 215/04  (2006.01)

(52) U.S. Cl. ..................... 546/165; 546/176; 546/181
(58) Field of Classification Search ................. 546/165, 546/176, 181
See application file for complete search history.

(56) References Cited

U.S. PATENT DOCUMENTS 5,965,572 A   10/1999   Ellis et al.

7,498,343 B2 *   3/2009   Van Gestel et al. .......... 514/312

FOREIGN PATENT DOCUMENTS

WO   WO 00/34265 A2   6/2000
WO   WO 2004/011436 A1   2/2004

OTHER PUBLICATIONS

Stella, V., et al. "Prodrugs: Do They Have Advantages in Clinical Practice?", Drugs vol. 29 (1985) pp. 455-473.
Stella, V. et al. "Prodrugs: The Control of Drug Delivery Via Bioreversible Chemical Modification" (1980) pp. 112-176.

* cited by examiner

*Primary Examiner*—D. Margaret Seaman
*Assistant Examiner*—Nizal S Chandrakumar

(57) ABSTRACT

The present invention relates to novel substituted quinoline derivatives according to the general Formula (I)

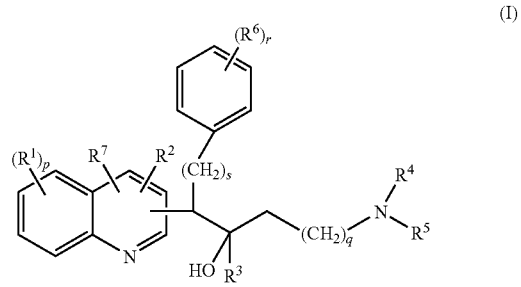

and pharmaceutically acceptable addition salts thereof, wherein the variable moieties are as defined in the specification. The invention also relates to a method of treating of mycobacterial diseases through administration of the claimed compounds and a process for preparing the claimed compounds.

18 Claims, No Drawings

MYCOBACTERIAL INHIBITORS

The present invention relates to novel substituted quinoline derivatives useful for the treatment of mycobacterial diseases, particularly those diseases caused by pathogenic mycobacteria such as *Mycobacterium tuberculosis, M. bovis, M. avium* and *M. marinum*.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death to one out of every three people with HIV/AIDS worldwide.

Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and can not be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against MDR strains.

The purpose of the present invention is to provide novel compounds, in particular substituted quinoline derivatives, having the property of inhibiting growth of mycobacteria and therefore useful for the treatment of mycobacterial diseases, particularly those diseases caused by pathogenic mycobacteria such as *Mycobacterium tuberculosis, M. bovis, M. avium, M. smegmatis* and *M. marinum*.

Substituted quinolines were already disclosed in U.S. Pat. No. 5,965,572 (The United States of America) for treating antibiotic resistant infections and in WO 00/34265 to inhibit the growth of bacterial microorganisms. WO 2004/011436 describes quinoline derivatives as antimycobacterial agents.

SUMMARY OF THE INVENTION

The present invention relates to novel substituted quinoline derivatives according to Formula (I).

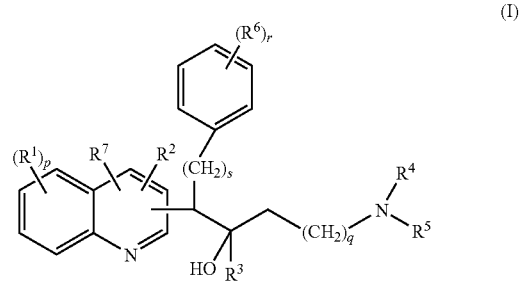

(I)

the pharmaceutically acceptable acid or base addition salts thereof, the quaternary amines thereof, the stereochemically isomeric forms thereof, the tautomeric forms thereof and the N-oxide forms thereof, wherein:
$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;
p is an integer equal to 1, 2 or 3;
s is an integer equal to zero, 1, 2, 3 or 4;
$R^2$ is hydrogen; halo; alkyl; hydroxy; mercapto; alkyloxy optionally substituted with amino or mono or di(alkyl) amino or a radical of formula

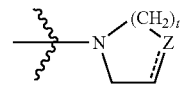

wherein Z is $CH_2$, $CH-R^8$, O, S, $N-R^8$ and t is an integer equal to 1 or 2 and the dotted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Ar; Het or a radical of formula

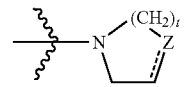

wherein Z is $CH_2$, $CH-R^8$, O, S, $N-R^8$; t is an integer equal to 1 or 2; and the dotted line represents an optional bond;
$R^3$ is alkyl, Ar, Ar-alkyl, Het or Het-alkyl;
q is an integer equal to zero, 1, 2, 3 or 4;

R⁴ and R⁵ each independently are hydrogen, alkyl or benzyl; or

R⁴ and R⁵ together and including the N to which they are attached may form a radical selected from the group of pyrrolidinyl, 2H-pyrrolyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each of said rings optionally being substituted with alkyl, halo, haloalkyl, hydroxy, alkyloxy, amino, mono or dialkylamino, alkylthio, alkyloxyalkyl, alkylthioalkyl and pyrimidinyl;

R⁶ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal R⁶ radicals may be taken together to form together with the phenyl ring to which they are attached a naphthyl;

r is an integer equal to 1, 2, 3, 4 or 5; and

R⁷ is hydrogen, alkyl, Ar or Het;

R⁸ is hydrogen, alkyl, hydroxyl, aminocarbonyl, mono- or di(alkyl)aminocarbonyl, Ar, Het, alkyl substituted with one or two Het, alkyl substituted with one or two Ar, Het-C(=O)— or Ar—C(=O)—;

alkyl is a straight or branched saturated hydrocarbon radical having from 1 to 6 carbon atoms or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, alkylcarbonyl, aminocarbonyl, morpholinyl and mono- or dialkylaminocarbonyl;

Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, isoquinolinyl, 1,2,3,4-tetrahydroisoquinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms;

provided that when the radical

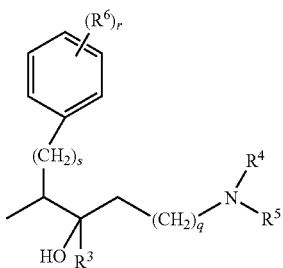

is placed in position 3 of the quinoline moiety; R⁷ is placed in position 4 of the quinoline moiety and R² is placed in position 2 of the quinoline moiety and represents hydrogen, hydroxy, mercapto, alkyloxy, alkyloxyalkyloxy, alkylthio, mono or di(alkyl)amino or a radical of formula

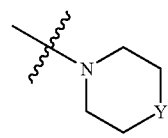

wherein Y is CH₂, O, S, NH or N-alkyl;
then s is 1, 2, 3 or 4.

DETAILED DESCRIPTION

In the framework of this application, alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo. Preferably, alkyl is methyl, ethyl or cyclohexylmethyl. More preferably alkyl is $C_{1-6}$alkyl which as a group or part of a group encompasses the straight and branched chain saturated hydrocarbon radicals having from 1 to 6 carbon atoms such as, methyl, ethyl, butyl, pentyl, hexyl, 2-methylbutyl and the like.

In the framework of this application, Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl. Preferably, Ar is naphthyl or phenyl, each optionally substituted with 1 or 2 halo substituents.

In the framework of this application, Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, isoquinolinyl, 1,2,3,4-tetrahydroisoquinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy. Preferably Het is thienyl.

In the framework of this application, halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms. Preferably, halo is bromo, fluoro or chloro and preferably, haloalkyl is trifluoromethyl.

In the framework of this application, the quinoline moiety is numbered as follows

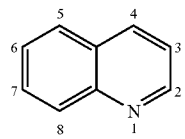

The

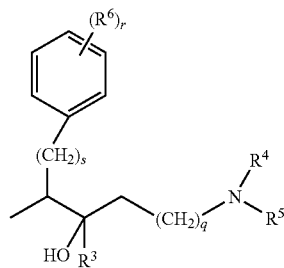

radical, $R^2$, $R^7$ and $R^1$ may be placed on any available position of the quinoline moiety.

Whenever used hereinafter, the term "compounds of formula (I)" or any subgroup thereof, is meant to also include their N-oxide forms, their salts, their quaternary amines, their tautomeric forms and their stereochemically isomeric forms. Of special interest are those compounds of formula (I) which are stereochemically pure.

An interesting embodiment of the present invention relates to those compounds of formula (I), the pharmaceutically acceptable acid or base addition salts thereof, the stereochemically isomeric forms thereof, the tautomeric forms thereof and the N-oxide forms thereof, wherein
  $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;
  p is an integer equal to 1, 2 or 3;
  s is an integer equal to zero, 1, 2, 3 or 4;
  $R^2$ is hydrogen; halo; alkyl; hydroxy; mercapto; alkyloxy optionally substituted with amino or mono or di(alkyl)amino or a radical of formula

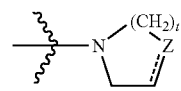

wherein Z is $CH_2$, $CH-R^8$, O, S, $N-R^8$ and t is an integer equal to 1 or 2 and the dotted line represents an optional bond; alkyloxyalkyloxy; alkylthio; mono or di(alkyl)amino wherein alkyl may optionally be substituted with one or two substituents each independently selected from alkyloxy or Ar or Het or morpholinyl or 2-oxopyrrolidinyl; Het or a radical of formula

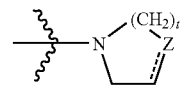

wherein Z is $CH_2$, $CH-R^8$, O, S, $N-R^8$; t is an integer equal to 1 or 2; and the dotted line represents an optional bond;
  $R^3$ is alkyl, Ar, Ar-alkyl, Het or Het-alkyl;
  q is an integer equal to zero, 1, 2, 3 or 4;
  $R^4$ and $R^5$ each independently are hydrogen, alkyl or benzyl; or
  $R^4$ and $R^5$ together and including the N to which they are attached may form a radical selected from the group of pyrrolidinyl, 2H-pyrrolyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, optionally substituted with alkyl, halo, haloalkyl, hydroxy, alkyloxy, amino, mono- or dialkylamino, alkylthio, alkyloxyalkyl, alkylthioalkyl and pyrimidinyl;
  $R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl; or
  two vicinal $R^6$ radicals may be taken together to form together with the phenyl ring to which they are attached a naphthyl;
  r is an integer equal to 1, 2, 3, 4 or 5; and
  $R^7$ is hydrogen, alkyl, Ar or Het;
  $R^8$ is hydrogen, alkyl, aminocarbonyl, mono- or di(alkyl)aminocarbonyl, Ar, Het, alkyl substituted with one or two Het, alkyl substituted with one or two Ar, Het-C(=O)—
  alkyl is a straight or branched saturated hydrocarbon radical having from 1 to 6 carbon atoms; or is a cyclic saturated hydrocarbon radical having from 3 to 6 carbon atoms or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;
  Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, alkylcarbonyl, aminocarbonyl, morpholinyl and mono- or dialkylaminocarbonyl;
  Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms, provided that when the radical

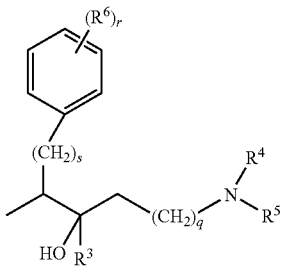

is placed in position 3 of the quinoline moiety; $R^7$ is placed in position 4 of the quinoline moiety and $R^2$ is placed in position 2 of the quinoline moiety and represents hydrogen, hydroxy, mercapto, alkyloxy, alkyloxyalkyloxy, alkylthio, mono or di(alkyl)amino or a radical of formula

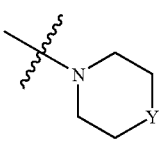

wherein Y is $CH_2$, O, S, NH or N-alkyl;

then s is 1, 2, 3 or 4.

Preferably, the invention relates to compounds of formula (I) or any subgroup thereof, as described hereinabove, provided that when the radical

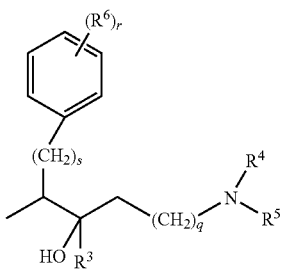

is placed in position 3 of the quinoline moiety; $R^7$ is placed in position 4 of the quinoline moiety and $R^2$ is placed in position 2 of the quinoline moiety, then s is 1, 2, 3 or 4.

Preferably, the invention relates to compounds of formula (I) or any subgroup thereof, as described hereinabove, provided that when the radical

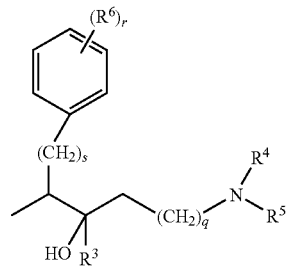

is placed in position 3 of the quinoline moiety; then s is 1, 2, 3 or 4.

Preferably, the invention relates to compounds of formula (I) or any subgroup thereof, as described hereinabove, provided that the radical

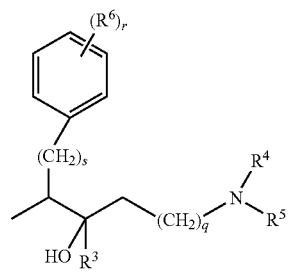

is not placed in position 3 of the quinoline moiety.

Preferably, the invention relates to compounds of formula (I) or any subgroup thereof, as described hereinabove, wherein the compounds have the following formula

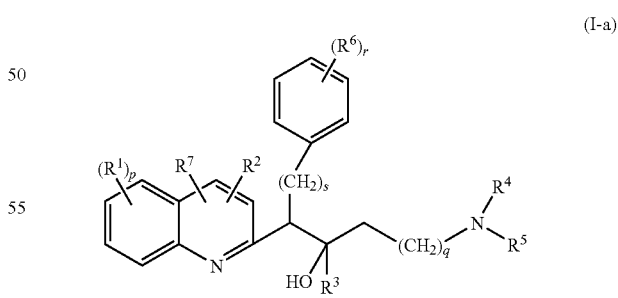

(I-a)

the pharmaceutically acceptable acid or base addition salts thereof the quaternary amines thereof, the stereochemically isomeric forms thereof, the tautomeric forms thereof and the N-oxide forms thereof.

Preferably, the invention relates to compounds of formula (I-a-1) or any subgroup thereof, as described hereinabove

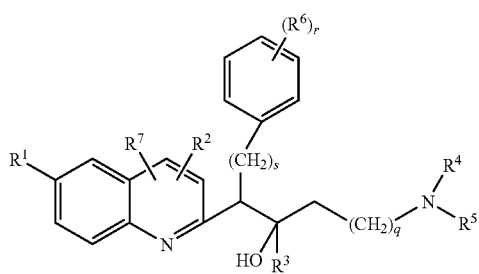

(I-a-1)

Preferably, the invention relates to compounds of formula (I-a-1-1) or any subgroup thereof, as described hereinabove

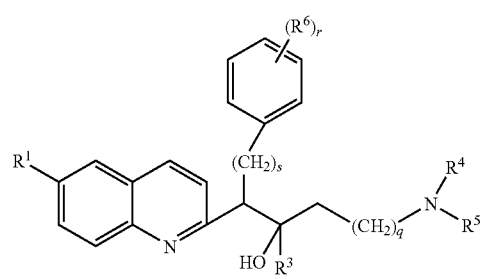

(I-a-1-1)

the pharmaceutically acceptable acid or base addition salts thereof, the quaternary amines thereof, the stereochemically isomeric forms thereof, the tautomeric forms thereof and the N-oxide forms thereof.

Preferably, the invention relates to compounds of formula (I) or any subgroup thereof, as described hereinabove, wherein the compounds have the following formula

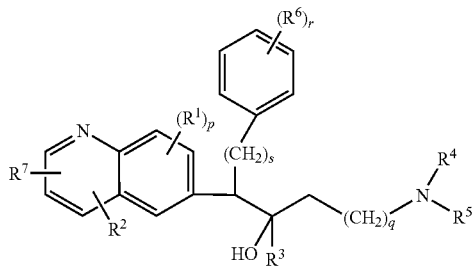

(I-b)

the pharmaceutically acceptable acid or base addition salts thereof, the quaternary amines thereof, the stereochemically isomeric forms thereof, the tautomeric forms thereof and the N-oxide forms thereof.

Preferably, the invention relates to compounds of formula (I) or any subgroup thereof, as described hereinabove, wherein the compounds have the following formula

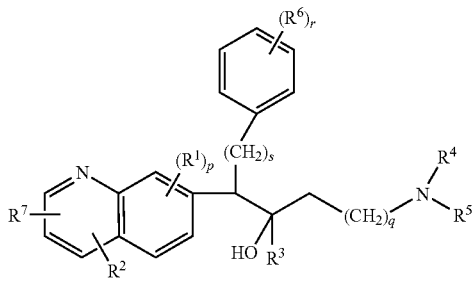

(I-c)

the pharmaceutically acceptable acid or base addition salts thereof, the quaternary amines thereof, the stereochemically isomeric forms thereof, the tautomeric forms thereof and the N-oxide forms thereof.

Preferably, the invention relates to compounds of Formula (I) or any subgroup thereof, as described hereinabove, wherein:

$R^1$ is hydrogen, halo, cyano, Ar, Het, alkyl, and alkyloxy;

p is an integer equal to 1, 2, 3 or 4; in particular 1 or 2; more in particular 1;

s is an integer of 0 or 1;

$R^2$ is hydrogen; alkyl; hydroxy; alkyloxy optionally substituted with amino or mono or di(alkyl)amino or a radical of formula

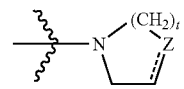

wherein Z is $CH_2$, $CH-R^{10}$, O, S, $N-R^{10}$ and t is an integer equal to 1 or 2 and the dotted line represents an optional bond; alkyloxyalkyloxy; alkylthio, mono or di(alkyl)amino; Ar; Het or a radical of formula

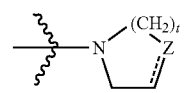

wherein Z is $CH_2$, $CH-R^{10}$, O, S, $N-R^{10}$; t is an integer equal to 1 or 2; and the dotted line represents all optional bond; in particular $R^2$ is hydrogen, hydroxy, alkyloxy, alkyloxyalkyloxy, alkylthio or a radical of formula

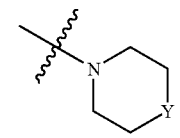

wherein Y is O; more in particular $R^2$ is hydrogen, halo or alkyl, even more in particular $R^2$ is hydrogen or alkyl;

$R^3$ is alkyl, Ar, Ar-alkyl or Het; in particular Ar;

q is an integer equal to zero, 1, 2, or 3; in particular 1;

$R^4$ and $R^5$ each independently are hydrogen, alkyl or benzyl; or

R⁴ and R⁵ together and including the N to which they are attached may form a radical selected from the group of pyrrolidinyl, imidazolyl, triazolyl, piperidinyl, piperazinyl, pyrazinyl, morpholinyl and thiomorpholinyl, optionally substituted with alkyl and pyrimidinyl; in particular R⁴ and R⁵ are alkyl; more in particular R⁴ and R⁵ are $C_{1-6}$alkyl, preferably methyl;

R⁶ is hydrogen, halo or alkyl; or two vicinal R⁶ radicals may be taken together to form together with the phenyl ring to which they are attached a naphthyl;

r is an integer equal to 1; and

R⁷ is hydrogen or Ar; in particular hydrogen or phenyl;

alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo or hydroxy;

Ar is a homocycle selected from the group of phenyl, naphthyl, acenaphthyl, tetrahydronaphthyl, each optionally substituted with 1, 2 or 3 substituents, each substituent independently selected from the group of halo, haloalkyl, cyano, alkyloxy and morpholinyl;

Het is a monocyclic heterocycle selected from the group of N-phenoxypiperidinyl, furanyl, thienyl, pyridinyl, pyrimidinyl; or a bicyclic heterocycle selected from the group of benzothienyl, 2,3-dihydrobenzo[1,4]dioxinyl or benzo[1,3]-dioxolyl; each monocyclic and bicyclic heterocycle may optionally be substituted on a carbon atom with 1, 2 or 3 alkyl substituents; and halo is a substituent selected from the group of fluoro, chloro and bromo.

For compounds according to Formula (I) or any subgroup thereof, as described hereinabove, preferably, R¹ is hydrogen, halo, Ar, Het, alkyl or alkyloxy. More preferably, R¹ is hydrogen, halo, Ar, alkyl or alkyloxy; even more preferably R¹ is halo. Most preferably, R¹ is bromo or chloro.

For compounds according to Formula (I) or any subgroup thereof as described hereinabove, preferably, p is equal to 1 or 2. More preferably, p is equal to 1.

For compounds according to Formula (I) or any subgroup thereof as described hereinabove, preferably, R² is hydrogen; halo, alkyl; hydroxy; mercapto; alkyloxy optionally substituted with amino or mono or di(alkyl)amino or a radical of formula

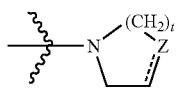

wherein Z is $CH_2$, CH—R⁸, O, S, N—R⁸ and t is an integer equal to 1 or 2 and the doted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Het or a radical of formula

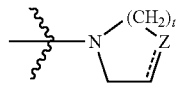

wherein Z is $CH_2$, CH—R⁸, O, S, N—R⁸; t is an integer equal to 1 or 2; and the dotted line represents an optional bond.

Also, an interesting group of compounds of Formula (I) or any subgroup thereof, as described hereinabove, are those compounds wherein R² is hydrogen; alkyl; alkyloxy optionally substituted with amino or mono or di(alkyl)amino or a radical of formula

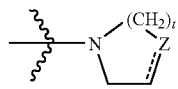

wherein Z is $CH_2$, CH—R¹⁰, O, S, N—R¹⁰ and t is an integer equal to 1 or 2 and the dotted line represents an optional bond; mono or di(alkyl)amino; Ar; Het or a radical of formula

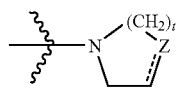

wherein Z is $CH_2$, CH—R¹⁰, O, S, N—R¹⁰; t is an integer equal to 1 or 2; and the dotted line represents an optional bond. More preferably, R² is hydrogen, halo, alkyl, alkyloxy or alkylthio. Even more preferably, R² is hydrogen, halo or $C_{1-6}$alkyl (e.g. ethyl). Most preferably, R² is hydrogen or $C_{1-6}$alkyl (e.g. ethyl).

For compounds according to Formula (I) or any subgroup thereof, as described hereinabove, preferably, R³ is naphthyl, phenyl or Het, each optionally substituted with 1 or 2 substituents, that substituent preferably being a halo or haloalkyl, most preferably being a halo. More preferably, R³ is optionally substituted naphthyl or optionally substituted phenyl. Most preferably, R³ is naphthyl or optionally substituted phenyl (e.g. 3-halophenyl or 3,5-dihalophenyl).

For compounds according to Formula (I) or any subgroup thereof, as described hereinabove, q is equal to zero, 1 or 2. More preferably, q is equal to 1.

For compounds according to Formula (I) or any subgroup thereof, as described hereinabove, R⁴ and R⁵ each independently are hydrogen or alkyl, more preferably hydrogen, or $C_{1-6}$alkyl, e.g. methyl or ethyl, most preferably methyl.

For compounds according to Formula (I) or any subgroup thereof, as described hereinabove, R⁴ and R⁵ together and including the N to which they are attached form a radical selected from the group of imidazolyl, triazolyl, piperidinyl, piperazinyl and thiomorpholinyl, optionally substituted with alkyl, halo, haloalkyl, hydroxy, alkyloxy, alkylthio, alkyloxyalkyl or alkylthioalkyl, preferably substituted with alkyl, most preferably substituted with methyl or ethyl.

For compounds according to Formula (I) or any subgroup thereof, as described hereinabove, R⁶ is hydrogen, halo, haloalkyl, hydroxy, Ar, alkyl, alkyloxy, alkylthio, alkyloxyalkyl, alkylthioalkyl, Ar-alkyl or di(Ar)alkyl. More preferably, R⁶ is hydrogen, alkyl or halo. Most preferably, R⁶ is hydrogen. Preferably r is 1 or 2. More preferably, r is 1.

For compounds according to Formula (I) or any subgroup thereof, as described hereinabove, preferably, R⁷ is hydrogen, methyl or Ar, more preferably hydrogen or Ar, e.g. phenyl.

For compounds according to Formula (I) or any subgroup thereof, as described hereinabove, preferably, R⁸ is hydrogen, alkyl, aminocarbonyl, mono- or di(alkyl)aminocarbonyl, Ar, Het, alkyl substituted with one or two Het, alkyl substituted with one or two Ar, Het-C(=O)—.

For compounds according to Formula (I) or any subgroup thereof, as described hereinabove, preferably, s is an integer equal to 0 or 1.

An interesting group of compounds of Formula (I) or any subgroup thereof, as defined hereinabove, are those compounds wherein
- R¹ is halo, in particular bromo;
- p is equal to 1;
- s is equal to 0 or 1;
- R² is hydrogen, halo or alkyl; in particular hydrogen or alkyl;
- R³ is optionally substituted phenyl or optionally substituted naphthyl, in particular 3-halophenyl, 3,5-dihalophenyl or naphthyl;
- R⁴ and R⁵ are $C_{1-6}$alkyl, in particular methyl.
- R⁶ is hydrogen and r is 1.
- R⁷ is hydrogen or Ar, in particular hydrogen or phenyl.

Interesting intermediates of the present invention are intermediates of formula (II)

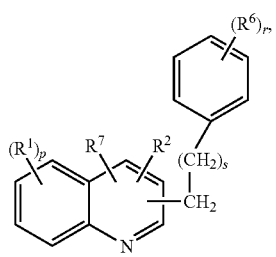

(II)

wherein R¹, R², R⁶, R⁷, p and s are as defined hereinabove, in particular interesting intermediates are intermediates of formula (II-a)

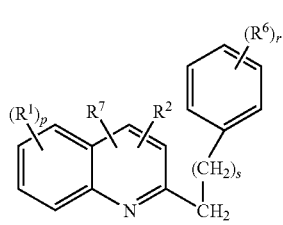

(II-a)

wherein R¹, R², R⁶, R⁷, p and s are as defined hereinabove.

The pharmaceutically acceptable acid addition salts are defined to comprise the therapeutically active non-toxic acid addition salt forms which the compounds according to Formula (I) or any subgroup thereof, as described hereinabove, are able to form. Said acid addition salts can be obtained by treating the base form of the compounds according to Formula (I) or any subgroup thereof, as described hereinabove, with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) or any subgroup thereof, as described hereinabove, containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to Formula (I) or any subgroup thereof, as described hereinabove, as well as the salts thereof, are able to form. Such solvates are, for example, hydrates and alcoholates.

The term "quaternary amine" as used hereinbefore defines the quaternary ammonium salts which the compounds of formula (I) or any subgroup thereof, as described hereinabove, are able to form by reaction between a basic nitrogen of a compound of formula (I) or any subgroup thereof, as described hereinabove, and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The term "stereochemically isomeric forms" as used herein defines all possible isomeric forms which the compounds of Formula (I) or any subgroup thereof, as described hereinabove, may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of Formula (I) or any subgroup thereof, as described hereinabove, are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "β" position of the mean plane determined by the ring system. The position of the highest priority substituent on the other asymmetric carbon atom in the ring system relative to the position of the highest priority substituent on the reference atom is denominated "β", if it is on the same side of the mean plane determined by the ring system, or "β", if it is on the other side of the mean plane determined by the ring system.

Compounds of Formula (I) or any subgroup thereof as described hereinabove, and some of the intermediate compounds invariably have at least one stereogenic centers in their structure which may lead to at least 2 stereochemically different structures.

The compounds of Formula (I) or any subgroup thereof as described hereinabove, as prepared in the processes described below may be synthesized in the form of racemic mixtures of enantiomers which can be separated from one another following art-known resolution procedures. The racemic compounds of Formula (I) or any subgroup thereof, as described hereinabove, may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) or any subgroup thereof, as described hereinabove, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of Formula (I) or any subgroup thereof, as described hereinabove, are meant to comprise those compounds of Formula (I) or any subgroup thereof, as described hereinabove, wherein e.g. an enol group is converted into a keto group (keto-enol tautomerism).

The N-oxide forms of the present compounds are meant to comprise the compounds of formula (I) or any subgroup thereof, as described hereinabove, wherein one or several tertiary nitrogen atoms are oxidized to the so-called N-oxide.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and *Drugs*, 1985, 29, pp. 455-473.

Pro-drugs forms of the pharmacologically-active compounds according to the invention will generally be compounds according to Formula (I) or any subgroup thereof, as described hereinabove, the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a C$_{1-6}$alkyl, phenyl, benzyl or one of the following groups:

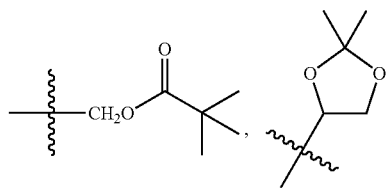

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds according to the invention have surprisingly been shown to be suitable for the treatment of mycobacterial diseases, particularly those diseases caused by pathogenic mycobacteria, including drug resistant and multi drug resistant mycobacteria, such as *Mycobacterium tuberculosis, M. bovis, M. avium, M. smegmatis* and *M. marinum*. The present invention thus also relates to compounds of Formula (I) or any subgroup thereof, as described hereinabove, as defined hereinabove, the pharmaceutically acceptable acid or base addition salts thereof, the stereochemically isomeric forms thereof, the tautomeric forms thereof and the N-oxide forms thereof, for use as a medicine.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution.

Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredient of formula (I) or any subgroup thereof, as described hereinabove, and, from 1 to 99.95% by weight, more preferably from 30 to 99.9 weight % of a pharmaceutically acceptable carrier, all percentages being based on the total composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Further, the present invention also relates to the use of a compound of Formula (I) or any subgroup thereof, as described hereinabove, the pharmaceutically acceptable acid or base addition salts thereof, the stereochemically isomeric forms thereof, the tautomeric forms thereof and the N-oxide forms thereof, as well as any of the aforementioned pharmaceutical compositions thereof for the manufacture of a medicament for the prevention or the treatment of mycobacterial diseases.

Accordingly, in another aspect, the invention provides a method of treating a patient suffering from, or at risk of, a mycobacterial disease, which comprises administering to the patient a therapeutically effective amount of a compound or pharmaceutical composition according to the invention.

The compounds of the present invention may also be combined with one or more other antimycobacterial agents.

Therefore, the present invention also relates to a combination of (a) a compound of formula (I) or any subgroup thereof, as described hereinabove, and (b) one or more other antimycobacterial agents.

The present invention also relates to a combination of (a) a compound of formula (I) or any subgroup thereof, as described hereinabove, and (b) one or more other antimycobacterial agents for use as a medicine.

A pharmaceutical composition comprising a pharmaceutically acceptable carrier and, as active ingredient, a therapeutically effective amount of (a) a compound of formula (I) or any subgroup thereof, as described hereinabove, and (b) one or more other antimycobacterial agents is also comprised by the present invention.

The other Mycobacterial agents which may be combined with the compounds of formula (I) or any subgroup thereof, as described hereinabove, are for example rifampicin (=rifampin); isoniazid; pyrazinamide; amikacin; ethionamide; moxifloxacin; ethanbutol; streptomycin; para-aminosalicylic acid; cycloserine; capreomycin; kanamycin; thioacetazone; PA-824; quinolones/fluoroquinolones such as for example ofloxacin, ciprofloxacin, sparfloxacin; macrolides such as for example clarithromycin, clofazimine, amoxycillin with clavulanic acid; rifamycins; rifabutin; rifapentine.

Preferably, the present compounds of formula (I) or any subgroup thereof, as described hereinabove, are combined with rifapentin and moxifloxacin.

General Preparation

The compounds according to the invention can generally be prepared by a succession of steps, each of which is known to the skilled person.

Compounds of formula (I) can be prepared by reacting an intermediate of formula (II) with an intermediate of formula (III) in the presence of a suitable coupling agent, such as for example n-butyl lithium, secBuLi, and in the presence of a suitable solvent, such as for example tetrahydrofuran, and optionally in the presence of a suitable base, such as for example 2,2,6,6-tetramethylpiperidine, $NH(CH_2CH_2CH_3)_2$, N,N-diisopropylamine or trimethylethylenediamine.

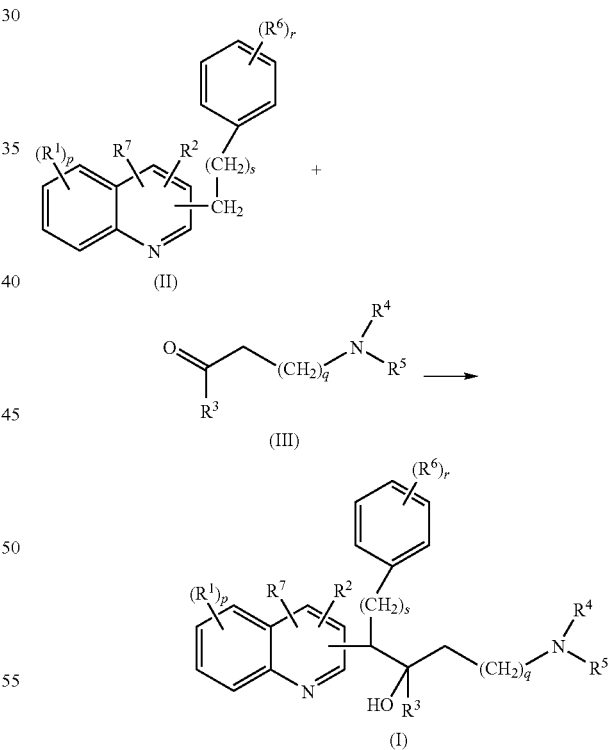

In the above reaction, the obtained compound of formula (I) can be isolated, and, if necessary, purified according to methodologies generally known in the art such as, for example, extraction, crystallization, distillation, trituration and chromatography. In case the compound of formula (I) crystallizes out, it can be isolated by filtration. Otherwise, crystallization can be caused by the addition of an appropriate solvent, such as for example water; acetonitrile; an alcohol, such as for example methanol, ethanol; and combinations of said solvents. Alternatively, the reaction mixture can also be evaporated to dryness, followed by purification of the residue by chromatography (e.g. reverse phase HPLC, flash chromatography and the like). The reaction mixture can also be purified by chromatography without previously evaporating the solvent. The compound of formula (I) can also be isolated by evaporation of the solvent followed by recrystallisation in an appropriate solvent, such as for example water; acetonitrile; an alcohol, such as for example methanol; and combinations of said solvents.

The person skilled in the art will recognise which method should be used, which solvent is the most appropriate to use or it belongs to routine experimentation to find the most suitable isolation method.

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^1$ represents halo, can be converted into a compound of formula (I) wherein $R^1$ represents Het, e.g. pyridyl, by reaction with

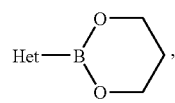

in the presence of a suitable catalyst, such as for example $Pd(PPh_3)_4$, a suitable solvent, such as for example dimethylether or an alcohol, e.g. methanol and the like, and a suitable base, such as for example disodium carbonate or dipotassium carbonate.

Compounds of formula (I) wherein $R^1$ represents halo, can also be converted into a compound of formula (I) wherein $R^1$ represents methyl, by reaction with $Sn(CH_3)_4$ in the presence of a suitable catalyst, such as for example $Pd(PPh_3)_4$, a suitable solvent, such as for example toluene.

Some of the compounds of formula (I) and some of the intermediates in the present invention may consist of a mixture of stereochemically isomeric forms. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

It is to be understood that in the above or the following preparations, the reaction products may be isolated from the reaction medium and, if necessary, further purified according to methodologies generally known in the art such as, for example, extraction, crystallization, distillation, trituration and chromatography.

Some of the intermediates and starting materials are known compounds and may be commercially available or may be prepared according to art-known procedures.

Intermediates of formula (II) wherein the

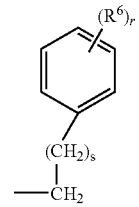

radical is placed in position 2 of the quinoline ring, s is an integer equal to 1 and position 4 of the quinoline ring is unsubstituted, said intermediates being represented by formula (II-a), can be prepared by reacting an intermediate of formula (IV) with phenyloxybenzene in the presence of ethyl acetate.

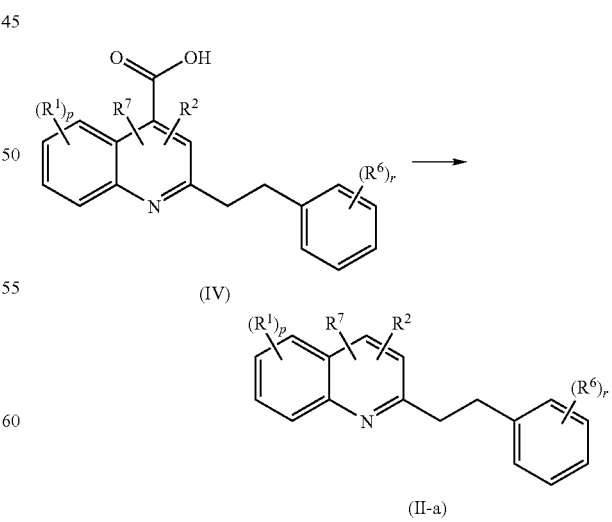

Intermediates of formula (IV) wherein $R^2$ and $R^7$ represent hydrogen, said intermediates being represented by formula (IV-a), can be prepared by reacting an intermediate of formula (V) with an intermediate of formula (VI) in the presence of a suitable base, such as for example sodium hydroxide.

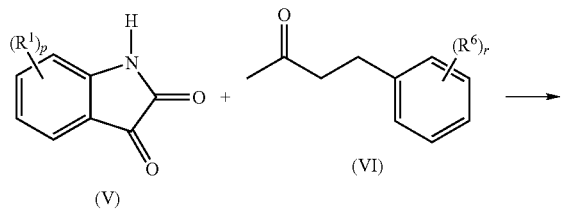

(V)      (VI)

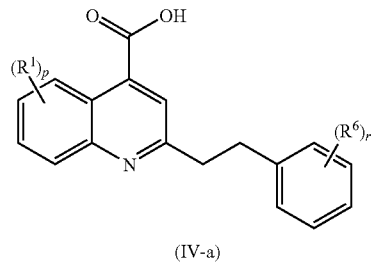

(IV-a)

Intermediates of formula (II) wherein the

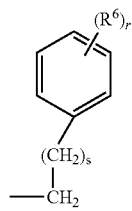

radical is placed in position 2 of the quinoline ring and s is 0, said intermediates being represented by formula (II-b), can be prepared by reacting an intermediate of formula (VII) wherein $W_1$ represents a suitable leaving group, such as for example halo, e.g. chloro and the like, with an intermediate of formula (VIII) wherein $W_2$ represents a suitable leaving group, such as for example halo, e.g. chloro, bromo and the like, in the presence of Zn, chlorotrimethylsilane, 1,2-dibromoethane and $Pd(PPh_3)_4$ and a suitable solvent such as for example tetrahydrofuran.

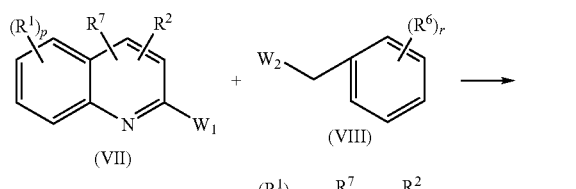

(VII)      (VIII)

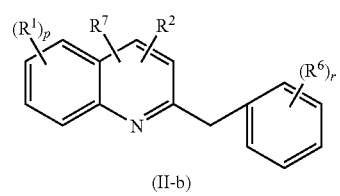

(II-b)

Intermediates of formula (VII) wherein $W_1$ represents chloro, said intermediates being represented by formula (VII-a), can be prepared by reacting an intermediate of formula (IX) with $POCl_3$.

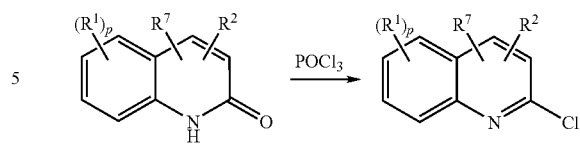

(IX)      (VII-a)

Intermediates of formula (IX) can be prepared by reacting an intermediate of formula (X) with 4-methylbenzenesulfonyl chloride in the presence of a suitable solvent, such as for example methylene chloride, and a suitable base, such as for example dipotassium carbonate.

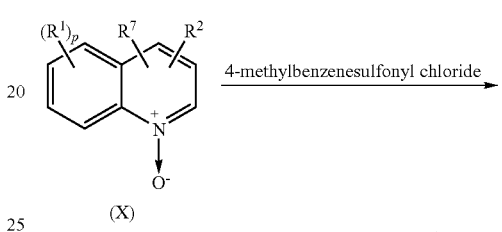

(X)

(IX)

Intermediates of formula (X) can be prepared by reacting an intermediate of formula (XI) with a suitable oxidizing agent, such as for example 3-chlorobenzenecarboperoxoic acid, in the presence of a suitable solvent, such as for example methylene chloride.

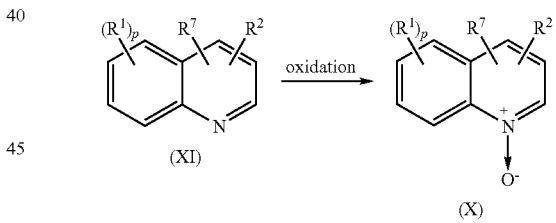

(XI)      (X)

Intermediates of formula (II) wherein s is 0, said intermediates being represented by formula (I-c), can be prepared by reacting an intermediate of formula (XII) with $Et_3SiH$ in the presence of a suitable acid, such as for example trifluoroacetic acid, and a suitable solvent, such as for example methylene chloride.

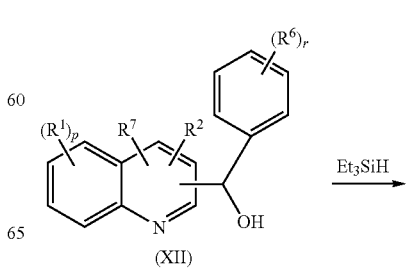

(XII)

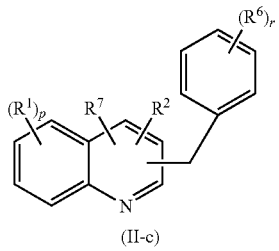

(II-c)

Intermediates of formula (XII) can be prepared by reacting an intermediate of formula (XIII) wherein $W_3$ represents a suitable leaving group, such as for example halo, e.g. chloro or bromo and the like, with an intermediate of formula (XIV) in the presence of a suitable coupling agent, such as for example n-butyl lithium, secBuLi, and in the presence of a suitable solvent, such as for example tetrahydrofuran, and optionally in the presence of a suitable base, such as for example 2,2,6,6-tetramethylpiperidine, $NH(CH_2CH_2CH_3)_2$, N,N-diisopropylamine or trimethylethylenediamine.

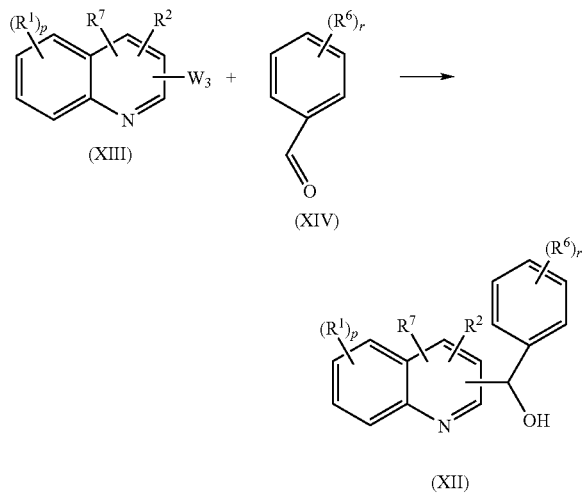

Intermediates of formula (XII) wherein radical is placed in position 8 of the quinoline ring, $R^2$ is placed in position 2, $R^7$ is placed in position 4 and $R^1$ is placed in position 6 of the quinoline ring, said intermediates being represented by formula (XII-a), can be prepared by reacting an intermediate of formula (XV) with an intermediate of formula (XIV) in the presence of a suitable coupling agent, such as for example n-butyl lithium, secBuLi, and in the presence of a suitable solvent, such as for example tetrahydrofuran, and optionally in the presence of a suitable base, such as for example 2,2,6,6-tetramethylpiperidine, $NH(CH_2CH_2CH_3)_2$, N,N-diisopropylamine or trimethylethylenediamine.

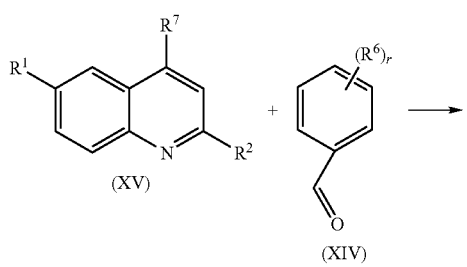

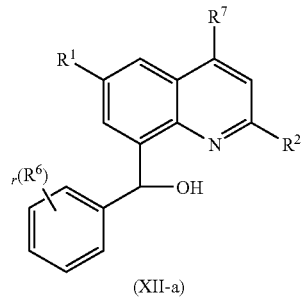

(XII-a)

Intermediates of formula (III) are compounds that are either commercially available or may be prepared according to conventional reaction procedures generally known in the art. For example, intermediate compounds of Formula (III) wherein q is equal to 1, said intermediates being represented by formula (III-a), can be prepared according to the following reaction scheme (1).

Scheme 1

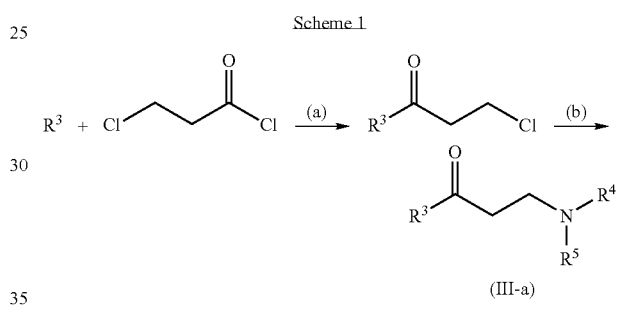

(III-a)

Reaction scheme (1) comprises step (a) in which an appropriately $R^3$ is reacted by Friedel-Craft reaction with an appropriate acylchloride such as 3-chloropropionyl chloride or 4-chlorobutyryl chloride, in the presence of a suitable Lewis acid, such as $AlCl_3$, $FeCl_3$, $SnCl_4$, $TiCl_4$ or $ZnCl_2$ and a suitable reaction-inert solvent, such as methylene chloride or ethylene dichloride. The reaction may conveniently be carried out at a temperature ranging between room temperature and reflux temperature. In a next step (b) an amino group (e.g. $—NR^4R^5$) is introduced by reacting the intermediate compound obtained in step (a) with an appropriate amine.

Intermediates of formula (III) can also be prepared by reacting an intermediate of formula (XVI) and an intermediate of formula (XVII) with formaldehyde in the presence of a suitable solvent, such as for example an alcohol, e.g. ethanol, and a suitable acid, e.g. HCl.

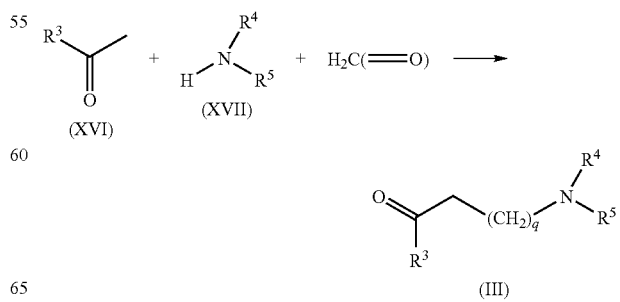

(III)

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC. Typically, compounds of Formula (I) may be separated into their isomeric forms.

The following examples illustrate the present invention without being limited thereto.

EXPERIMENTAL PART

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction, The isolation method is described in detail below.

For some of the final compounds, stereochemical configurations are indicated in the structures. These configurations are relative configurations indicating that the groups concerned are located in the same or opposite plane of the molecule ( ⧹⧹=same plane; ⧹⧽=opposite plane)

Hereinafter, "DIPE" is defined as diisopropyl ether, "THF" is defined as tetrahydrofurane, "HOAc" is defined as acetic acid, "EtOAc" is defined as ethylacetate.

A. Preparation of the Intermediate Compounds

Example A1

Preparation of Intermediate 1 and Intermediate 2

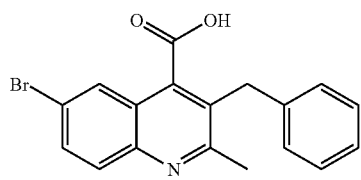

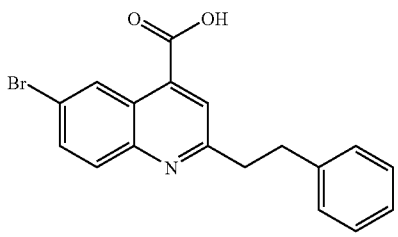

A mixture of 5-bromo-1H-indole-2,3-dione (0.221 mol) in NaOH 3N (500 ml) was stirred at 80° C. for 30 minutes and then cooled to room temperature. 4-Phenyl-2-butanone (0.221 mol) was added. The mixture was stirred and refluxed for 90 minutes, cooled to room temperature and acidified with HOAc until pH=5. The precipitate was filtered off, washed with $H_2O$ and dried. Yield: 75 g (95%) of a mixture of intermediate 1 and intermediate 2.

Example A2

Preparation of Intermediate 3

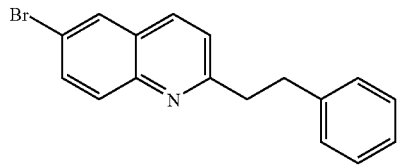

A mixture of intermediate 1 and intermediate 2 (0.21 mol) in 1,1'-oxybis[benzene] (600 ml) was stirred at 300° C. for 12 hours. EtOAc was added. The mixture was extracted three times with HCl 6N, basified with $K_2CO_3$ solid and extracted with $CH_2Cl_2$. The organic layer was separated, dried ($MgSO_4$), filtered and the solvent was evaporated. The residue (36 g) was purified by column chromatography over silica gel (eluent: $CH_2CH_2/CH_3OH$ 99/1; 15-40 µm). The pure fractions were collected and the solvent was evaporated. Yield: 11 g (16%) of intermediate 3.

Example A3

Preparation of Intermediate 4

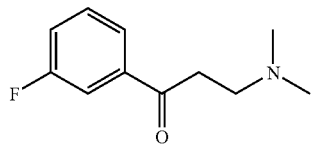

A mixture of 1-(3-fluorophenyl)ethanone (0.195 mol), formaldehyde (0.235 mol) and $NH(CH_3)_2$.HCl (0.235 mol) in ethanol (300 ml) and HCl conc. (1 ml) was stirred and refluxed overnight, then brought to room temperature. The precipitate was filtered, washed with ethanol and dried. The mother layer was evaporated. The residue was taken up in diethyl ether. The precipitate was filtered, washed with diethyl ether and dried. This fraction was taken up in $K_2CO_3$ 10%. The precipitate was washed with $CH_2CH_2$ and dried. Yield: 18.84 g (49%) of intermediate 4.

Example A4 a. Preparation of Intermediate 5

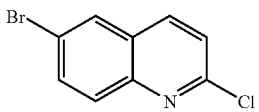

A mixture of 6-bromo-2(1H)-quinolinone (0.089 mol) in $POCl_3$ (55 ml) was stirred at 60° C. overnight, then at 100° C. for 3 hours and the solvent was evaporated. The residue was taken up in $CH_2Cl_2$, poured out into ice waters basified with $NH_4OH$ concentrated, filtered over celite and extracted with $CH_2Cl_2$. The organic layer was separated, dried ($MgSO_4$), filtered and the solvent was evaporated. Yield: 14.5 g of intermediate 5 (67%).

b. Preparation of Intermediate 6

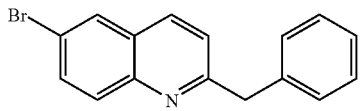

A mixture of Zn (0.029 mol) and 1,2-dibromoethane (0.001 mol) in THF (6 ml) was stirred and refluxed for 10 minutes, then cooled to room temperature. Chlorotrimethylsilane (0.001 mol) was added. The mixture was stirred at room temperature for 30 minutes. A solution of bromomethylbenzene (0.025 mol) in THF (25 ml) was added dropwise at 5° C. for 90 minutes. The mixture was stirred at 0° C. for 2 hours. A solution of intermediate 5 (prepared according to A4.a) (0.021 mol) in THF (75 ml) was added. $Pd(PPh_3)_4$ (0.0008 mol) was added. The mixture was stirred and refluxed for 2 hours, then cooled to room temperature, poured out into $NH_4Cl$ 10% and extracted with EtOAc. The organic layer was washed with $H_2O$, then with satured NaCl, dried ($MgSO_4$), filtered, and the solvent was evaporated. The residue (12 g) was purified by column chromatography over silica gel (eluent: cyclohexane/$CH_2Cl_2$ 50/50; 20-45 μm). Two fractions were collected and the solvent was evaporated. Yield of the second fraction. 2.5 g of intermediate 6.

Example A5 a. Preparation of Intermediate 7

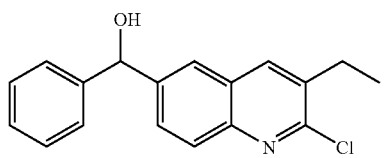

nBuLi (1.6 M) (0.066 mol) was added dropwise at –50° C. to a mixture of 6-bromo-2-chloro-3-ethylquinoline (0055 mol) in THF (150 ml). The mixture was stirred at 50° C. for 1 hour. A solution of benzaldehyde (0.066 mol) in THF (70 ml) was added at –70° C. The mixture was stirred at –70° C. for 1 hour, poured out into $H_2O$ at 0° C. and extracted with EtOAc. The organic layer was separated, dried ($MgSO_4$), filtered, and the solvent was evaporated. The residue (15 g) was crystallized from DIPE/iPrOH. The precipitate was filtered off and dried. Yield: 7.6 g of intermediate 7 (46%).

b. Preparation of Intermediate 8

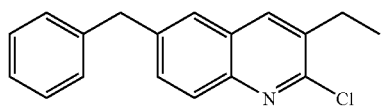

A mixture of intermediate 7 (prepared according to A5.a) (0.021 mol), $Et_3SiH$ (0.21 mol) and $CF_3COOH$ (0.21 mol) in $CH_2Cl_2$ (100 ml) was stirred at room temperature for 3 days. $H_2O$ was added. The mixture was extracted with $CH_2Cl_2$. The organic layer was separated, washed with $K_2CO_3$ 10%, dried over magnesium sulfate, filtered and the solvent was evaporated. The residue (8 g) was purified by column chromatography over silica gel (eluent: cyclohexane/AcOEt 95/5; 15-40 μm). The pure fractions were collected and the solvent was evaporated. Yield: 3.8 g (64%, m.p.: 66° C.).

Example A6 a. Preparation of Intermediate 9

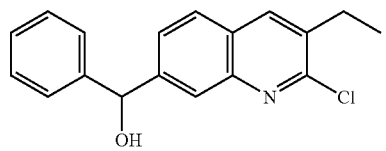

n-Butyl lithium (0.055 mol) was added slowly at –70° C. to a mixture of 7-bromo-2-chloro-3-ethylquinoline (0.37 mol) in THF (100 ml) under $N_2$ flow. The mixture was stirred for 2 hours, then a solution of benzaldehyde (0.055 mol) in THF (55 ml) was added. The mixture was stirred for 3 hours, water was added at –20° C. and the mixture was extracted with EtOAc. The organic layer was separated, dried over magnesium sulfate, filtered and the solvent was evaporated. The residue (12.2 g) was purified by column chromatography over silica gel (eluent: cyclohexane/AcOEt 80/20; 15-40 μm). The pure fractions were collected and the solvent was evaporated. Yield: 6.1 g of intermediate 9 (56%).

b. Preparation of Intermediate 10

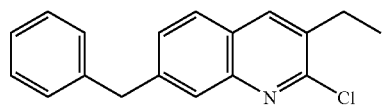

A mixture of intermediate 9 (prepared according to A6.a) (0.0205 mol), $Et_3SiH$ (0.205 mol) and $CF_3COOH$ (0.205 mol) in $CH_2CH_2$ (300 ml) was stirred at room temperature for 7 days. $H_2O$ was added. The mixture was extracted with $CH_2Cl_2$. The organic layer was separated, washed with $K_2CO_3$ 10%, dried over magnesium sulfate, filtered and the solvent was evaporated. The residue (7.1 g) was purified by column chromatography over silica gel (eluent:cyclohexane/AcOEt 95/5; 15-40 μm). The pure fractions were collected and the solvent was evaporated. Yield: 4.8 g of intermediate 10 (83%).

Example A7 a. Preparation of Intermediate 11

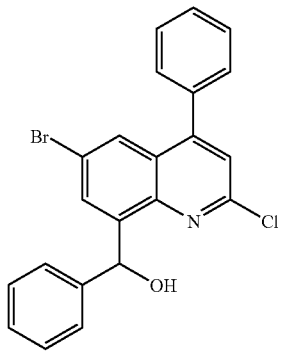

n-Butyl lithium (0.0090 mol) was added slowly at −20° C. to a mixture of 2,2,6,6-tetramethylpiperidine (0.0090 mol) in THF (15 mL) under $N_2$ flow. The mixture was stirred for 20 minutes, then cooled to −70° C. A solution of 6-bromo-2-chloro-4-phenylquinoline (0.0060 mol) in THF (40 mL) was added. The mixture was stirred for 1 hour. A solution of benzaldelhyde (0.0090 mol) in THF (15 ml) was added. The mixture was stirred for 1 hour at −70° C. then 3 hours at room temperature. $H_2O$ was added. The mixture was extracted with EtOAc. The organic layer was separated, dried over magnesium sulfate, filtered and the solvent was evaporated. The residue (3.0 g) was purified by column chromatography over silica gel (eluent: cyclohexane/AcOEt: 95/5; 15-40 μm). The pure fractions were collected and the solvent was evaporated. Yield: 1.8 g of intermediate 11 (71%).

b. Preparation of Intermediate 12

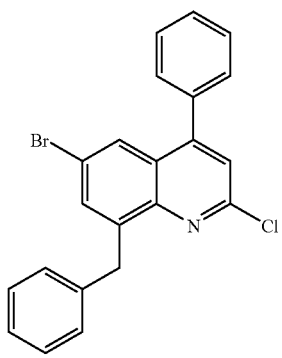

A mixture of intermediate 11 (prepared according to A7.a) (0.0042 mol), $Et_3SiH$ (0.0424 mol) and $CF_3COOH$ (0.0424 mol) in $CH_2Cl_2$ (100 ml) was stirred at room temperature for 24 hours. $H_2O$ was added. The mixture was extracted with $CH_2Cl_2$. The organic layer was separated, washed with $K_2CO_3$ 10%, dried over magnesium sulfate, filtered and the solvent was evaporated. The residue (1.3 g) was crystallized from DIPE. The precipitate was filtered off and dried. Yield: 0.66 g (38%, m.p.: 121° C.)

B. Preparation of the Final Compounds

Example B1

Preparation of Compound 1 and Compound 4

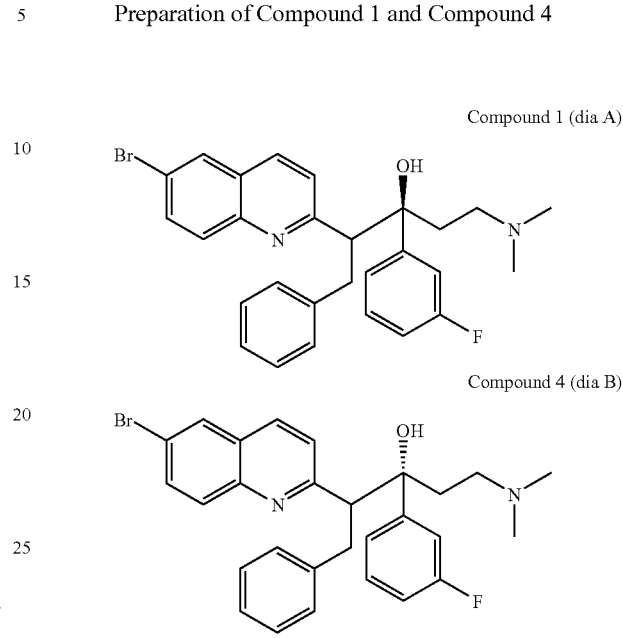

nBuLi 1.6M (0.0072 mol) was added at −20° C. to a mixture of N-(1-methylethyl)-2-propanamine.hydrochloride (1:1) (0.0071 mol) in THF (25 ml) under nitrogen stream. The mixture was stirred for 20 minutes then cooled to −70° C. A solution of intermediate 3 (0.0061 mol) in THF (5 ml) was added. The mixture was stirred for 2 hours. A solution of intermediate 4 (0.0061 mol) in THF (5 ml) was added at −70° C. The mixture was stirred at −70° C. for 3 hours. $NH_4Cl$ 10% was added. The mixture was extracted with EtOAc. The organic layer was separated, dried ($MgSO_4$), filtered, and the solvent was evaporated. The residue (3.4 g) was purified by column chromatography over silica gel (eluent: $CH_2CH_2$/$CH_3OH$/$NH_4OH$ 97/3/0.1; 15-40 μm). Two fractions were collected and the solvent was evaporated. The first residue (0.9 g) was crystallized from diisopropyl ether. The precipitate was filtered off and dried. Yield: 0.49 g of compound 1 (diastereoisomer A) (m.p.: 136° C.). The second residue (0.79 g) was crystallized from diisopropyl ether. The precipitate was filtered off and dried. Yield: 0.105 g of compound 4 (diastereoisomer B) (m.p.: 179° C.).

Example B2

Preparation of Compound 2 and Compound 3

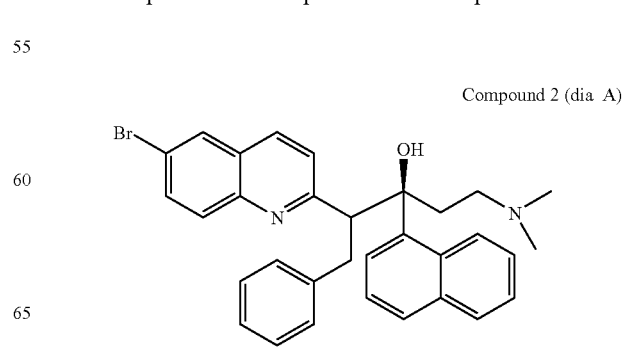

-continued

Compound 3 (dia B)

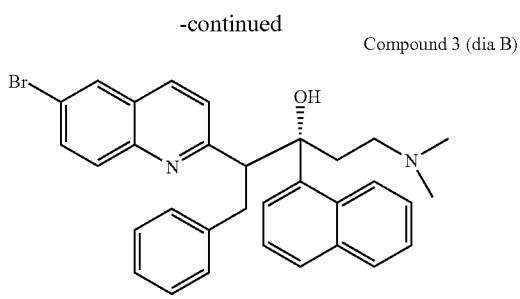

nBuLi 1.6M (0.0072 mol) was added dropwise at −20° C. to a solution of N-(1-methylethyl)-2-propanamine.hydrochloride (1:1) (0.0071 mol) in THF (25 ml) under nitrogen stream. The mixture was stirred for 20 minutes. Then cooled to −70° C. A solution of intermediate 3 (0.0061 mol) in THF (5 ml) was added. The mixture was stirred for 2 hours. A solution of 3-(dimethylamino)-1-(1-naphthalenyl)-1-propanone (0.0062 mol) in THF (5 ml) was added at −70° C. The mixture was stirred at −70° C. for 3 hours. $NH_4Cl$ 10% was added. The mixture was extracted with EtOAc. The organic layer was separated, dried ($MgSO_4$), filtered, and the solvent was evaporated. The residue (4 g) was purified by column chromatography over silica gel (eluent: $CH_2Cl_2/CH_3OH/NH_4OH$ 97/3/0.1; 15-40 µm). Two fractions were collected and the solvent was evaporated. The first residue (0.61 g) was crystallized from DIPE. The precipitate was filtered off and dried. Yield: 0.303 g of compound 2 (diastereoisomer A) (m.p. 143° C.). The second residue (0.56 g) was purified by column chromatography over silica gel (eluent: $CH_2Cl_2/CH_3OH$ 98/2). The pure fractions were collected and the solvent was evaporated. Yield: 0.104 g of compound 3 (diastereoisomer 1) (m.p.: 69° C.).

Example B3

Preparation of Compound 5 and 6

Compound 5 (dia A)

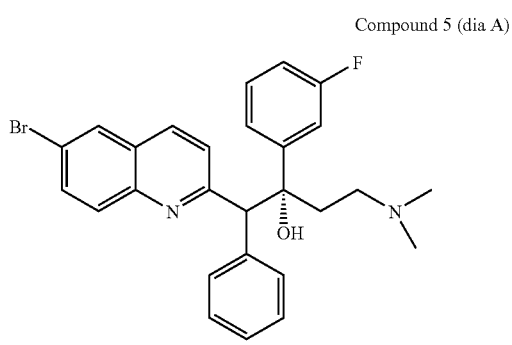

Compound 6 (dia B)

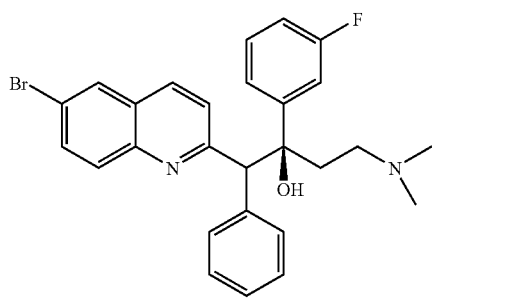

n-BuLi 1.6M (0.0048 mol) was added at −70° C. to a mixture of N-(1-methylethyl)-2-propanamine (0.0049 mol) in THF (15 ml). The mixture was stirred at −20° C. for 20 minutes. A solution of intermediate 6 (prepared according to A4.b) (0.004 mol) in THF (5 ml) was added at −70° C. The mixture was stirred at −70° C. for 2 hours. A solution of intermediate 4 (prepared according to A3) (0.004 mol) in THF (5 ml) was added at −70° C. The mixture was stirred at −70° C. for 3 hours. $NH_4Cl$ 10% was added. The mixture was extracted with EtOAc. The organic layer was separated, dried ($MgSO_4$), filtered, and the solvent was evaporated. Yield: 2.1 g. This fraction was purified by column chromatography over silica gel (eluent: $CH_2Cl_2/CH_3OH/NH_4OH$ 96.5/3.5/0.1; 15-40 µm). Two fractions were collected and the solvent was evaporated. Yield: 0.123 g of fraction A and 0.122 g of fraction B. Fraction A was purified by column chromatography over silica gel (eluent: $CH_2Cl_2/CH_3OH$ 98/2; 15-40 µm). The pure fractions were collected and the solvent was evaporated. Yield: 0.119 g. This fraction was taken up in $iPr_2O$/pentane. The mixture was evaporated. Yield: 0.077 g of compound 5 (mp.: 58° C.). Fraction B was crystallized from DIPE. The precipitate was filtered off and dried. Yield: 0.039 g of compound 6 (mp.: 134° C.).

Example B4

Preparation of Compound 13 and 14

Compound 13 (dia A)

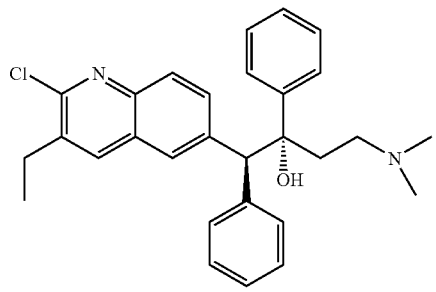

Compound 14 (dia B)

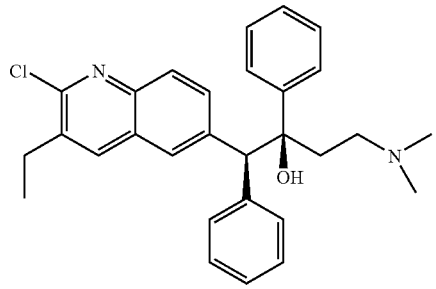

n-BuLi 1.6M (0.013 mol) was added at −20° C. to a mixture of N-(1-methylethyl)-2-propanamine (0.013 mol) in THF (25 ml) under N₂ flow. The mixture was stirred at −20° C. for 20 minutes, then cooled to −70° C. A solution of intermediate 8 (prepared according to A5.b) (0.0106 mol) in THF (25 ml) was added. The mixture was stirred at −70° C. for 45 minutes. A solution of 3-(dimethylamino)-1-(1-naphthalenyl)-1-propanone (0.013 mol) in THF (20 ml) was added. The mixture was stirred at −70° C. for 2 hours, poured out into H₂O at −30° C. and extracted with EtOAc. The organic layer was separated, dried (MgSO₄), filtered, and the solvent was evaporated. The residue (5.5 g) was purified by column chromatography over silica get (eluent: CH₂Cl₂/CH₃OH/NH₄OH 99/1/0.1; 15-40 µm). Two fractions were collected and the solvent was evaporated. Yield: 0.33 g of compound 13 (diastereoisomer A) (3%) and 0.11 g of compound 14 (diastereoisomer B) (1%).

Following compound was prepared according to the above procedure. The purification of the residue (*) is indicated because different from the above-described purification.

-continued

Compound 8 (diastereoisomer B)

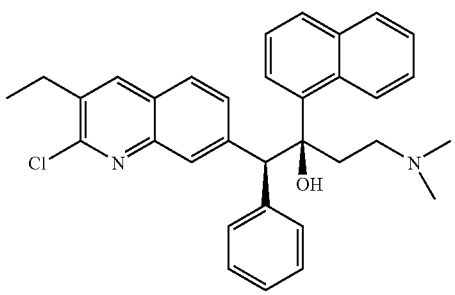

n-Butyl lithium (0.0043 mol) was added slowly at −20° C. to a mixture of diisopropyl amine (0.0043 mol) in THF (10 ml) under N₂ flow. The mixture was stirred for 20 minutes, then cooled to −70° C. A solution of intermediate 10 (prepared according to A6.b) (0.0036 mol) in THF (10 ml) was added. The mixture was stirred for 2 hours. A solution of

| | | |
|---|---|---|
| compound 15 | The residue (5.4 g) was purified by column chromatography over silica gel (eluent: CH₂Cl₂/CH₃OH 98/2; 15-40 µm). The pure fractions were collected and the solvent was evaporated. Yield: 0.17 g of compound 15 (mixture of diastereoisomer A and diastereoisomer B: 45/55) (3%). | 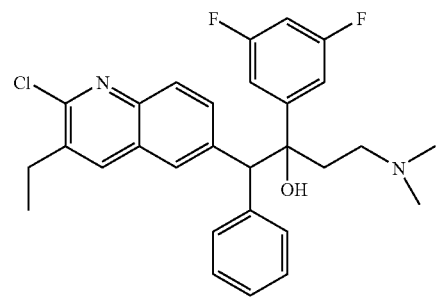<br>Compound 15 (A/B 45/55) |

Example B5

Preparation of Compound 7 and 8

3-(dimethylamino)-1-(1-naphthalenyl)-1-propanone (0.0043 mol) in THF (10 ml) was added. The mixture was stirred for 2 hours. H₂O was added. The mixture was extracted with EtOAc. The organic layer was separated, dried over magnesium sulfate, filtered and the solvent was evaporated. The residue (*) (1.8 g) was purified by column chromatography over silica gel (eluent: CH₂Cl₂/MeOH/NH₄OH 98/2/0.2; 1-40 µm). Two fractions were collected and the solvent was evaporated. Yield: 0.17 g of fraction 1 and 0.15 g of fraction 2. Fraction 1 was crystallized from MeOH. The precipitate was filtered off and dried. Yield: 0.082 g of compound 7 (5%, diastereoisomer A). Fraction 2 was purified by column chromatography over silica gel (eluent: CH₂Cl₂/MeOH: 98/2; 15-40 µm). The pure fractions were collected and the solvent was evaporated. Yield: 0.13 g of compound 8 (7%, diastereoisomer B).

Following compounds were prepared according to the above procedure. The purification of the residue (*) is indicated because different from the above-described purification.

Compound 7 (diastereoisomer A)

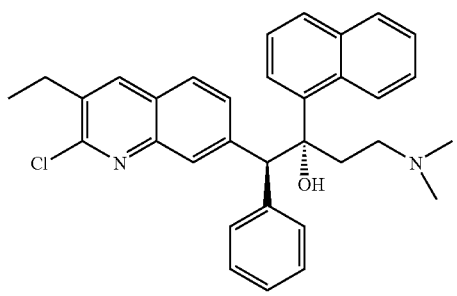

| compound 9 and compound 10 | The residue (1.9 g) was purified by column chromatography over silica gel (eluent: CH$_2$Cl$_2$/MeOH: 99/1; 15-40 μm). Two fractions were collected and the solvent was evaporated. Yield: Fraction 1: 0.42 g of diastereoisomer A and fraction 2: 0.31 g (18%) of compound 9 (diastereoisomer B). Fraction 1 was crystallized from CH$_3$OH. The precipitate was filtered off and dried. Yield: 0.22 g of compound 10 (diastereoisomer A) (13%; m.p.: 185° C.). | 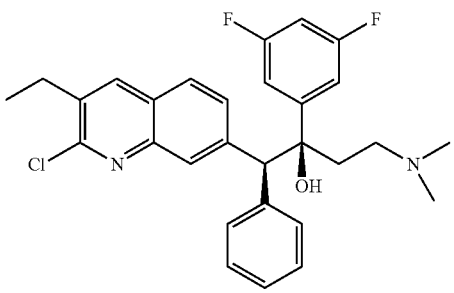<br>Compound 10 (diastereoisomer A)<br><br>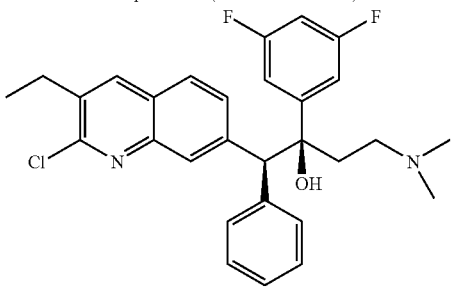<br>Compound 9 (diastereoisomer B) |
|---|---|---|

Example B6

Preparation of Compound 11 and 12

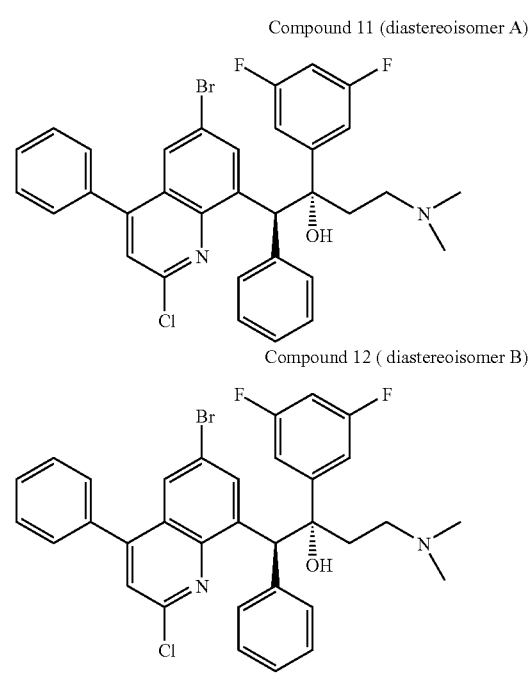

Compound 11 (diastereoisomer A)

Compound 12 (diastereoisomer B)

n-Butyl lithium (0.002 mol) was added slowly at −20° C. to a mixture of diisopropyl amine (0.002 mol) in THF (5 mL) under N$_2$ flow. The mixture was stirred for 20 minutes, then cooled to −70° C. A solution of intermediate 12 (prepared according to A7.b) (0.0017 mol) in THF (7 ml) was added. The mixture was stirred for 2 hours. A solution of 1-(3,5-difluorophenyl)-3-dimethylamino-1-propanone (−(0.002 mol) in THF (4 ml) was added. The mixture was stirred for 2 hours. H$_2$O was added. The mixture was extracted with EtOAc. The organic layer was separated, dried over magnesium sulfate, filtered and the solvent was evaporated. The residue (1.1 g) was purified by column chromatography over silica gel (eluent: CH$_2$Cl$_2$/MeOH: 9911; 15-40 μm). Two fractions were collected and the solvent was evaporated. Yield: 0.061 g of fraction 1 and 0.070 g of fraction 2. Fraction 1 was crystallized from MeOH. The precipitate was filtered off and dried. Yield: 0.046 g of compound 11 (5%, m.p.: 220° C., diastereoisomer A). Fraction 2 was crystallized from MeOH. The precipitate was filtered off and dried. Yield: 0.053 g (5%, m.p.: 216° C., diastereoisomer B).

C. Analytical Methods

The mass of the compounds was recorded with LCMS (liquid chromatography mass spectrometry). Three methods were used which are described below. The data are gathered in Table 1 below.

LCMS-Method 1

LCMS analysis was carried out (electrospray ionization in positive mode, scanning mode from 100 to 900 amu) on a Kromasil C18 column (Interchim, Montluçon, FR; 5 μm, 4.6×150 mm) with a flow rate of 1 ml/minute. Two mobile phases (mobile phase A: 30% 6.5 mM ammonium acetate+ 40% acetonitrile+30% formic acid (2 ml/l); mobile phase B: 100% acetonitrile) were employed to run a gradient condition from 100% A for 1 minute to 100% B in 4 minutes, 100% B for 5 minutes to 100% A in 3 minutes, and reequilibrate with 100% A for 2 minutes.

LCMS-Method 2

LCMS analysis was carried out (electrospray ionization in both positive and negative (pulsed) mode scanning from 100 to 1000 amu) on a Kromasil C18 column (Interchim, Montluçon, FR; 3.5 μm, 4.6×100 mm) with a flow rate of 0.8 ml/minute. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute.

TABLE 1

LCMS parent peak

| No. | MH+ | LCMS-method |
|---|---|---|
| Compound 7 | 509 | 1 |
| compound 9 | 495 | 2 |
| compound 15 | 495 | 1 |
| compound 13 | 509 | 1 |
| compound 14 | 509 | 1 |

D. Pharmacological Examples

D.1. In-Vitro Method for Testing Compounds Against *M. Tuberculosis*

Flat-bottom, sterile 96-well plastic microtiter plates were filled with 100 µl of Middlebrook (1×) broth medium. Subsequently, stock solutions (10× final test concentration) of compounds were added in 25 µl volumes to a series of duplicate wells in column 2 so as to allow evaluation of their effects on bacterial growth. Serial five-fold dilutions were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Entreated control samples with (column 1) and without (column 12) inoculum were included in each microtiter plate. Approximately 5000 CFU per well of Mycobacterium tuberculosis (strain H37RV), in a volume of 100 µl in Middlebrook (1×) broth medium, was added to the rows A to H, except column 12. The same volume of broth medium without inoculum was added to column 12 in row A to H. The cultures were incubated at 37° C. for 7 days in a humidified atmosphere (incubator with open air valve and continuous ventilation). One day before the end of incubation, 6 days after inoculation, Resazurin (1:5) was added to all wells in a volume of 20 µl and plates were incubated for another 24 hours at 37° C. On day 7 the bacterial growth was quantitated fluorometrically.

The fluorescence was read in a computer-controlled fluorometer (Spectramax Gemini EM, Molecular Devices) at an excitation wavelength of 530 nm and an emission wavelength of 590 nm. The percentage growth inhibition achieved by the compounds was calculated according to standard methods, and MIC data (representing IC90's expressed in microgram/ml) were calculated.

D.2. In-Vitro Method for Testing Compounds for Anti-Bacterial Activity Against Strain *M. Smegmatis* ATCC607

Flat-bottom, sterile 96-well plastic microtiter plates were filled with 180 µl of sterile deionized water, supplemented with 0.25% BSA. Subsequently, stock solutions (7.8× final test concentration) of compounds were added in 45 µl volumes to a series of duplicate wells in column 2 so as to allow evaluation of their effects on bacterial growth. Serial five-fold dilutions (45 µl in 180 µl) were made directly in the microtiter plates from column 2 to 11 using a customised robot system (Zymark Corp. Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 250 CFU per well of bacteria inoculum, in a volume of 100 µl in 2.8× Mueller-Hinton broth medium, was added to the rows A to H, except column 12. The same volume of broth medium without inoculum was added to column 12 in row A to H. The cultures were incubated at 37° C. for 48 hours in a humidified 5% $CO_2$ atmosphere (incubator with open air valve and continuous ventilation). At the end of incubation, two days after inoculation, the bacterial growth was quantitated fluorometrically. Therefore Alamar Blue (10×) was added to all wells in a volume of 20 µl and plates were incubated for another 2 hours at 50° C.

The fluorescence was read in a computer-controlled fluorometer (Cytofluor, Biosearch) at an excitation wavelength of 530 nm and an emission wavelength of 590 nm (gain 30). The % growth inhibition achieved by the compounds was calculated according to standard methods. The $pIC_{50}$ was defined as the 50% inhibitory concentration for bacterial growth. The results are shown in Table 2.

TABLE 2

Results of an in vitro-screening of the compounds according to the invention for *M. smegmatis* ($pIC_{50}$) and *M. tuberculosis* ($pIC_{50}$)

| Co. No. | *M. smegmatis* $pIC_{50}$ | *M. tuberculosis* $pIC_{50}$ |
|---|---|---|
| 1 | 6.2 | |
| 2 | 6.5 | |
| 3 | 5.7 | |
| 6 | 4.9 | |
| 15 | 6.4 | 5 |
| 10 | 5.9 | 5.1 |
| 14 | 5.9 | |
| 13 | 5.8 | |
| 9 | 5.8 | |
| 8 | 5.8 | |
| 11 | 5.7 | |

What is claimed is:
1. A compound according to the general Formula (I)

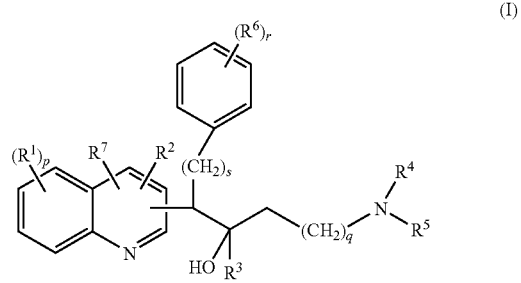

the pharmaceutically acceptable acid or base addition salts thereof, the stereochemically isomeric forms thereof, the tautomeric forms thereof and the N-oxide forms thereof, wherein:

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2 or 3;

s is an integer equal to zero, 1, 2, 3 or 4;

$R^2$ is hydrogen; halo; alkyl; hydroxy; mercapto; alkyloxy optionally substituted with amino or mono or di(alkyl)amino or a radical of formula

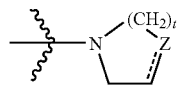

wherein Z is $CH_2$, CH—$R^8$, O, S, N—$R^8$ and t is an integer equal to 1 or 2 and the dotted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Ar; Het or a radical of formula

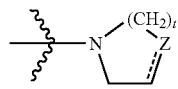

wherein Z is $CH_2$, CH—$R^8$, O, S, N—$R^8$; t is an integer equal to 1 or 2; and the dotted line represents an optional bond;

$R^3$ is alkyl, Ar, Ar-alkyl, Het or Het-alkyl;

q is an integer equal to zero, 1, 2, 3 or 4;

$R^4$ and $R^5$ each independently are hydrogen, alkyl or benzyl; or $R^4$ and $R^5$ together and including the N to which they are attached may form a radical selected from the group of pyrrolidinyl, 2H-pyrrolyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, each of said rings optionally being substituted with alkyl, halo, haloalkyl, hydroxy, alkyloxy, amino, mono- or dialkylamino, alkylthio, alkyloxyalkyl, alkylthioalkyl and pyrimidinyl;

$R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^6$ radicals may be taken together to form together with the phenyl ring to which they are attached a naphthyl;

r is an integer equal to 1, 2, 3, 4 or 5; and $R^7$ is hydrogen, alkyl, Ar or Het;

$R^8$ is hydrogen, alkyl, hydroxyl, aminocarbonyl, mono- or di(alkyl)aminocarbonyl, Ar, Het, alkyl substituted with one or two Het, alkyl substituted with one or two Ar, Het-C(=O)— or Ar—C(=O)—;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, alkylcarbonyl, aminocarbonyl, morpholinyl and mono- or dialkylaminocarbonyl;

Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, isoquinolinyl, 1,2,3,4-tetrahydroisoquinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms;

provided that when the radical

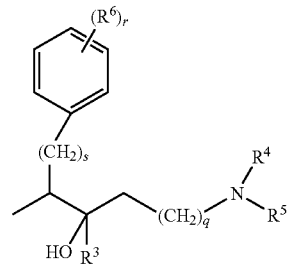

is placed in position 3 of the quinoline moiety; $R^7$ is placed in position 4 of the quinoline moiety and $R^2$ is placed in position 2 of the quinoline moiety and represents hydrogen, hydroxy, mercapto, alkyloxy, alkyloxyalkyloxy, alkylthio, mono or di(alkyl)amino or a radical of formula

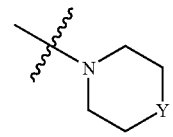

wherein Y is $CH_2$, O, S, NH or N-alkyl;

then s is 1, 2, 3 or 4.

2. A compound according to claim 1 wherein $R^2$ is hydrogen; halo; alkyl; hydroxy; mercapto; alkyloxy optionally substituted with amino or mono or di(alkyl)amino or a radical of formula

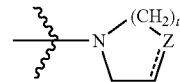

wherein Z is CH$_2$, CH—R$^8$, O, S, N—R$^8$ and t is an integer equal to 1 or 2 and the dotted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Het or a radical of formula

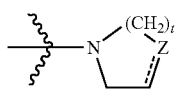

wherein Z is CH$_2$, CH—R$^8$, O, S, N—R$^8$; t is an integer equal to 1 or 2; and the dotted line represents an optional bond; R$^4$ and R$^5$ each independently are hydrogen, alkyl or benzyl; or R$^4$ and R$^5$ together and including the N to which they are attached may form a radical selected from the group of pyrrolidinyl, 2H-pyrrolyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, optionally substituted with alkyl, halo, haloalkyl, hydroxy, alkyloxy, amino, mono- or dialkylamino, alkylthio, alkyloxyalkyl, alkylthioalkyl and pyrimidinyl; R$^8$ is hydrogen, alkyl, aminocarbonyl, mono- or di(alkyl) aminocarbonyl, Ar, Het, alkyl substituted with one or two Het, alkyl substituted with one or two Ar, Het-C(=O)—; Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy.

3. A compound according to claim 1 provided that when the radical

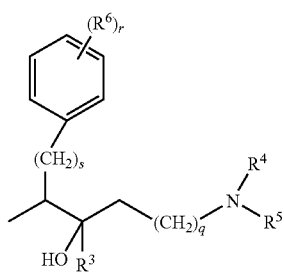

is placed in position 3 of the quinoline moiety; R$^7$ is placed in position 4 of the quinoline moiety and R$^2$ is placed in position 2 of the quinoline moiety, then s is 1, 2, 3 or 4.

4. A compound according to claim 1 wherein the compound is a compound of formula (I-a)

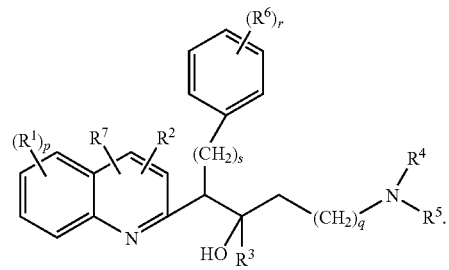

(I-a)

5. A compound according to claim 1 wherein the compound is a compound of formula (I-b).

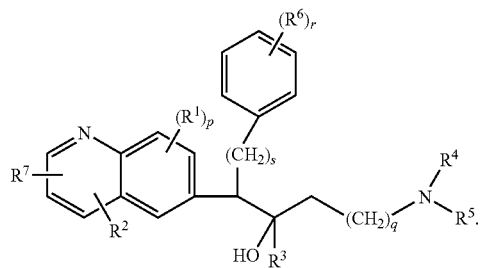

(I-b)

6. A compound according to claim 1 wherein the compound is a compound of formula (I-c).

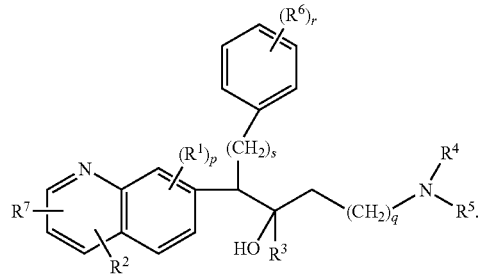

(I-c)

7. A compound according to claim 1 wherein R$^1$ is halo.

8. A compound according to claim 1 wherein p is equal to 1.

9. A compound according to claim 1 wherein R$^2$ is hydrogen, halo or C$_{1-6}$alkyl.

10. A compound according to claim 1 wherein R$^3$ is naphthyl or phenyl, each optionally substituted with 1 or 2 substituents, that substituent preferably being a halo.

11. A compound according to claim 1 wherein q is an integer equal to 1.

12. A compound according to claim 1 wherein R$^4$ and R$^5$ each independently are hydrogen or C$_{1-6}$alkyl.

13. A compound according to claim 1 wherein R$^6$ is hydrogen, alkyl or halo.

14. A compound according to claim 1 wherein R$^7$ is hydrogen or Ar.

15. A compound according to claim 1 wherein s is an integer equal to 0 or 1.

16. A composition comprising a pharmaceutically acceptable carrier and, as active ingredient, a therapeutically effective amount of a compound as defined in claim 1.

17. A method of treating a mycobacterial disease in a patient comprising administering an effective amount of a compound according to claim 1 to said patient.

18. A process for preparing a compound according to claim 1 characterized by reacting an intermediate of formula (II) with an intermediate of formula (III) in the presence of a suitable coupling agent and in the presence of a suitable solvent, and optionally in the presence of a suitable base,

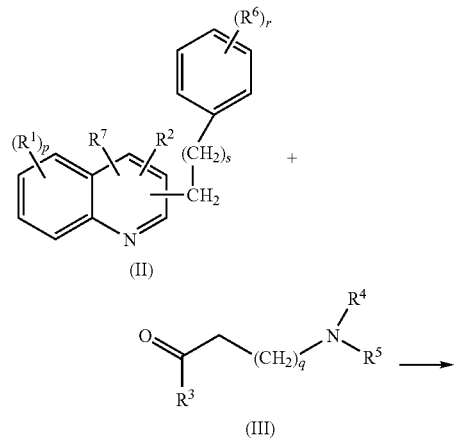

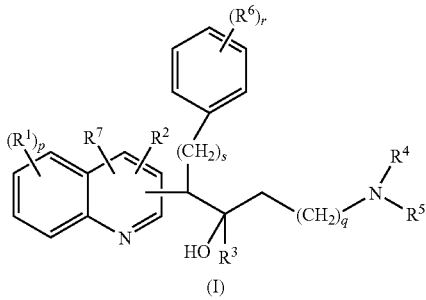

wherein $R^1$ to $R^7$, p, s, r and q are as defined in claim 1;

or, if desired, converting compounds of formula (Ia) or (Ib) into each other following art-known transformations, and further, if desired, converting the compounds of formula (Ia) or (Ib), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms, quaternary amines, tautomeric forms or N-oxide forms thereof.

* * * * *